United States Patent
Alvarez

(12)
(10) Patent No.: US 6,284,543 B1
(45) Date of Patent: Sep. 4, 2001

(54) RAPID PAPANICOLAOU STAINING METHOD FOR CERVICO-VAGINAL SPECIMENS

(76) Inventor: Iliana I. Alvarez, 229 Walker St., Babylon, NY (US) 11704

( * ) Notice: Subject to any disclaimer, the term of this patent is extended or adjusted under 35 U.S.C. 154(b) by 0 days.

(21) Appl. No.: 09/634,016

(22) Filed: Aug. 8, 2000

(51) Int. Cl.$^7$ .................................................. G01N 33/48
(52) U.S. Cl. ............................ 436/64; 436/63; 436/174; 435/40.5; 435/40.51
(58) Field of Search ................................ 436/63, 64, 164, 436/166, 174, 811, 813; 435/40.5, 40.51

(56) References Cited

U.S. PATENT DOCUMENTS

| | | | |
|---|---|---|---|
| 4,550,016 | * | 10/1985 | Harris ................................ 435/40.51 |
| 5,143,627 | * | 9/1992 | Lapidus et al. ...................... 210/767 |
| 5,318,795 | * | 6/1994 | Stokes et al. ............................ 427/4 |
| 6,143,512 | * | 11/2000 | Markovic et al. ...................... 435/21 |

OTHER PUBLICATIONS

Culling. *Handbook of Histopathological and Histochemical Techniques*, 3rd edition, pp. 491–192, 1974.*

* cited by examiner

*Primary Examiner*—Maureen M. Wallenhorst
(74) *Attorney, Agent, or Firm*—Lackenbach Siegel

(57) ABSTRACT

A method for staining a Pap test slide specimen for conventional Pap test and, particularly a ThinPrep Pap test specimen, in which a number of multiple hydrating, staining and dehydrating step are performed in an equal number of 10 to 15 dippings at about equal dip times of about 1 second. The total method time is 100 to 150 seconds. The specimen pre-staining fixative solution is a 10% buffered formalin solution and a 95% lower alcohol in a 1:2 volumetric ratio. The method simplifies the staining process and laboratory technician error, while providing an improved stain contrast with a clean background in the resultant conventional and ThinPrep Pap test stained specimens.

17 Claims, No Drawings

RAPID PAPANICOLAOU STAINING METHOD FOR CERVICO-VAGINAL SPECIMENS

BACKGROUND OF THE INVENTION

1. Field of the Invention

This invention relates to cell staining. Specifically this invention relates to staining a Pap slide specimen, including conventional smears and ThinPrep Pap test slides.

2. Background and Discussion of the Prior Art

Almost 5,000 women die each year from cervical cancer in the United States. The cervico-vaginal Papanicolaou test or Pap test is a powerful tool for detecting cancerous and precancerous cervical lesions. The Pap test smear has been credited with reducing mortality from cervical cancer by as much as 70%.

The Pap test involves a staining method. This staining method includes a polychromatic reaction which seeks to display the many variations of cellular morphology to show degrees of cellular maturity and metabolic activity. The four main steps of the Pap test staining method are: (1) slide fixation, (2) nuclear staining with hematoxylin, (3) cytoplasmic staining, generally with counterstains orange G and EA, and (4) clearing and mounting. The term "Pap staining method" or "Pap test staining method" as used hereinbefore and hereinafter throughout the specification refers generally to the aforesaid method.

The Pap test staining method has been generally used on conventional cervico-vaginal Pap smear specimens. The conventional Pap test smear however had false negative rates ranging from 10–15%, and up to 90% of those false negative rates were due to limitations of staining and slide preparation of such specimens. More recently the Cytyc Corporation developed the ThinPrep Pap test. Instead of smearing the cells on a slide, the cells are collected in a transport medium, from which a slide with a filter preparation is obtained for the test.

The art provided several complex Pap test staining methods involving multiple steps of greatly varying times and clippings. Certain prior art short versions of Pap test staining methods took an inordinate amount of time of upwards to 20 minutes or more and were complex, which readily invited error by the laboratory technician. Many of these prior art Pap test staining short methods were generally directed to fine needle aspirated (FNA) specimens and to the conventional cervico-vaginal smears, and not to the ThinPrep Pap test specimen.

One such conventional prior art short method which sought to reduce the overall time, was the "Quick Papanicolaou Staining Procedure for Stat Specimens" developed by the Johns Hopkins Cytopathology Laboratory, Baltimore, Md., as follows:

| | | |
|---|---|---|
| 1. | Tap water | 5–10 dips (until surface is smooth) |
| 2. | Gill's hematoxylin No. 2 | 1 min, including 10 initial dips |
| 3. | Tap water | 5 dips |
| 4. | Scott's tap water substitute | 15 sec |
| 5. | Tap water | 5 dips |
| 6. | Stat OG/EA | 1 min, including 10 initial dips |
| 7. | 95% ethanol | 5 dips |
| 8. | 95% ethanol | 5 dips |
| 9. | Absolute ethanol | 10 dips |
| 10. | Absolute ethanol | 10 dips |
| 11. | Xylene | 5 dips |
| 12. | Xylene Coverslip | 5 dips |

The Johns Hopkins' Method required 12 post-fixing, pre-coverslip steps, and took several minutes. The great disparity in procedure times for each step and sequence invited error by the laboratory technician and difficult the mechanization of the staining method.

Another attempt to reduce the Pap test staining method time was done specifically in connection with fine needle aspiration (FNA) specimens as disclosed in "Ultrafast Papanicolaou Stain—An Alternative Preparation for Fine Needle Aspiration Cytology" G. C. H. Yang and I. I. Alvarez, ACTA Cytol., vol. 39, no. 1, January–February 1995. The Yang-Alvarez FNA staining method was as follows:

| | |
|---|---|
| A. Alcoholic Formalin Fixative: | Mixture of 65% ethanol and 4% formaldehyde. It was convenient to make 3L of fixative from 300 mL of 38–40% formaldehyde, 2,053 mL of 95% ethanol and 647 mL of distilled water. |
| B. Staining Method: | |
| 1. Normal saline | 30 seconds |
| 2. 95% Ethanol (optional, for storage/transport) | |
| 3. Alcoholic formalin | 10 seconds |
| 4. Water | 6 slow dips |
| 5. Richard-Allan Hematoxylin 2 | 2 slow dips |
| 6. Water | 6 slow dips |
| 7. 95% Ethanol | 6 slow dips |
| 8. Richard-Allan Cytostain | 4 slow dips |
| 9. 95% Ethanol | 6 slow dips |
| 10. 100% Ethanol | 6 slow dips |
| 11. Xylene | 10 slow dips |
| Mount and coverslip | |

The Yang-Alvarez FNA staining method required a relatively complicated fixative mixture solution, 8 post-fixing, pre-coverslip steps, and provided improvement in the resultant stained specimen, but again the laboratory technician was faced with greatly disparate dipping sequences and times, and as such invited error. That is, the laboratory technician had to change from a 10 second fixing to a 6 dip hydrating and then to a 2 dip hematoxylin staining. These disparate sequencing times invited error. Further the Yang-Alvarez staining method was FNA specimen specific and not for cervico vaginal specimens.

One attempt was made to apply the Yang-Alvarez FNA approach to cervicovaginal smears as disclosed in "Ultrafast Papanicolaou Protocol for Cervicovaginal Smears," G. C. H. Yang et al., ASC Abstracts, Nov. 1, 1995. This modification of the Yang-Alvarez FNA staining method to cervicovaginal smears is as follows:

| | | |
|---|---|---|
| 1. | Dist. water | 3 min |
| 2. | Dist. water | 3 min |
| 3. | Dist. water | 3 min |
| 4. | Hexatox II | 20 sec |
| 5. | Tap water (discard dirty water | until clear |

-continued

| | | |
|---|---|---|
| | fill with clean water) | |
| 6. | 95% alcohol | 6 dips |
| 7. | Cytostain | 40 sec-5 min |
| 8. | 95% alcohol until clear (discard dirty alcohol, fill with clean alcohol) | |
| 9. | 100% alcohol | 6 dips |
| 10. | 100% alcohol | 6 dips |
| 11. | Xylene | 6 dips |
| 12. | Xylene | 6 dips |

The Yang et al adaption or modification of the Yang-Alvarez FNA staining method required 12 separate post-fixing, pre-coverslip steps, and also required more than 15 minutes, all in disparate sequence times ranging from a 6 dip step taking about 6 seconds to a cytostain staining step taking upwards of 5 minutes. Again this method was not laboratory technician friendly in that it invited errors because of the disparate dip sequencing as well as in the number of steps and in the disparate step times, and difficult the use of automatic stainer machines.

The art desired a simple, faster and laboratory technician friendly Pap test staining method. The art also desired a Pap test staining method used for conventional pap smears and which was particularly useful for ThinPrep Pap test specimens. The art further desired a Pap test staining method as aforesaid which consequently is adaptable for handling large numbers of Pap test slide specimens with minimal or no errors, and will facilitate the use of automatization for the staining method. The art still further required a method as aforesaid with an improved stained specimen, particularly an improvement in background and contrast stain quality. The present invention addresses and provides those art desired improvements.

SUMMARY OF THE INVENTION

A method for staining Pap test slide specimens for conventional pap test smears, and also particularly ThinPrep Pap test specimens, which method provides hydration, staining and dehydration steps of about the same number of dips and times. Each step is about 10 to 15 dips of about 1 second for each dip. The post staining dehydration requires at least about three separate alcohol steps with each step of the same 10 to 15 one second dips. The hematoxylin and cytostain staining steps are each also 10 to 15 one second dips. The present Pap test staining method requires only 10 post-fixation, precoverslip steps, with each step of minimal and yet equal times of about 10 to 15 seconds, with the overall time being from 100 to 150 seconds. The method is laboratory technician friendly in eliminating the step sequence time disparity and in reducing the sequence time and total time, and consequently the likelihood of error, which will facilitate the use or adaption of automatic stainer machines. The method also provides an improved stained specimen, particularly one of improved background and contrast stain quality.

The present invention is an improvement over the used Yang-Alvarez staining method for FNA which required a fixation step dependent on a mixture of pure formaldehyde (38–40%), water and alcohol; which could be a problem if the laboratory has only 10% buffered formaldehyde available. For example, some laboratory facilities do not carry or use pure or concentrated formaldehyde, for storage and handling safety reasons.

In another aspect, the present invention provides an improved fixation step, namely one in which a fixative solution of 10% buffered formalin and 95% lower alcohol in a 1:2 ratio is used. This improvement in the fixative solutions simplifies the process for the laboratory technician and also decreases the risk involved with handling concentrated formaldehyde.

DESCRIPTION OF THE PREFERRED EMBODIMENT

In one embodiment the present invention is a method for staining a Pap test slide specimen by sequentially:
(a) fixing the slide specimen;
(b) hydrating the slide specimen from step (a);
(c) staining the slide specimen from step (b) for at least about 10 to 15 seconds;
(d) hydrating the slide specimen from step (c);
(e) staining the slide specimen from step (d) for at least about 10 to 15 seconds; and
(f) dehydrating the slide specimen from step (e) in at least three sequential steps, and
particularly including where step (f) includes (f)(i) dehydrating with an alcohol for at least about 10 to 15 seconds; (f)(i) dehydrating with an alcohol for at least about 10 to 15 seconds; and (f)(iii) dehydrating with an alcohol for at least about 10 to 15 seconds.

In another embodiment the present invention is the method as aforesaid specifically with the steps being of equal time of about 10 to 15 seconds. The steps are accomplished by dipping in the respective medium or bath, with each dip taking about 1 second. The laboratory technician is trained to undertake these essentially unvarying 1 second dips, and can readily do so without inviting error. This is particularly so where, as in the present method there is an, equal number of sequential dips for each step.

More specifically, the present invention is a method for staining a Pap test slide specimen which includes the following steps:
(a) fixing the slide specimen with a 10% buffered formalin and 95% alcohol solution;
(b) dipping the slide specimen from step (a) in a first water bath 10–15 times, with each dip taking 1 second;
(c) dipping the slide specimen from step (b) in hematoxylin 10–15 times, with each dip taking 1 second;
(d) dipping the slide specimen form step (c) in a second water bat h 10–15 times, with each dip taking 1 second;
(e) dipping the slide specimen from step (d) in a first alcohol bath 10–15 times, with each dip taking 1 second;
(f) dipping the slide specimen from step (e) in a third water bath 10–15 times, with each dip taking 1 second;
(g) dipping the slide specimen from step (f) in cytostain 10–15 times, with each dip taking 1 second;
(h) dipping the slide specimen from step (f) in a second alcohol bath 10–15 times, with each dip taking 1 second;
(i) dipping the slide specimen for step (h) in a third alcohol bath 10–15 times, with each dip taking 1 second;
(j) dipping the slide specimen for step (i) in a fourth alcohol bath 10–15 times, with each dip taking 1 second; and
(k) dipping the slide specimen for step (j) in a low molecular weight organic solvent 10–15 times, with each dip taking 1 second.

Steps (h)–(j) provide three separate alcohol baths, with each step of the same 10 to 15 one second dips. Step (h) is preferably an alcohol solution of 95% alcohol, whereas steps (i) and (j) are preferably 100% alcohol baths.

In still another aspect the present invention is as aforesaid but specifically wherein the specimen is a ThinPrep Pap test specimen.

In still a further aspect the method is as aforesaid wherein the fixature solution is 10% buffered formalin and 95% lower alcohol in a volumetric ratio of 1:2.

The following example illustrates the invention.

EXAMPLE

A ThinPrep Pap test specimen was prepared according to the well known method developed by the Cytyc Corporation, Boxborough, Mass., and known in the art as the ThinPrep System. The ThinPrep Pap test specimen was prepared according to the ThinPrep System, as follows:

Step 1—A gynecologic sample was collected using a broom-type or cytobrush/spatula cervical sampling device.

Step 2—Instead of smearing the cells on a slide, the sampling device was rinsed into a ThinPrep vial containing PresevCyt® transport medium. The device is then discarded.

Step 3—The sample vial was capped, labeled, and sent to the laboratory for slide preparation.

Step 4—At the laboratory, the vial was placed into the ThinPrep 2000 Processor. First, a gentle dispersion step breaks up blood, mucous, non-diagnostic debris, and then thoroughly mixes the sample. A negative pressure pulse was generated which draws fluid through a TransCyt® Filter that collects a thin, even layer of diagnostic cellular material. The ThinPrep 2000 Processor constantly monitored the rate of flow through the TransCyt Filter during the collection process to prevent the cellular presentation from being too scant or too dense. The cellular material was then transferred to a glass slide.

A fixative solution was prepared using 10% buffered formalin and 95% ethanol in a 1:2 volumetric ratio. The afore-described ThinPrep Pap test specimen was dipped into the aforesaid fixative solution 10 times with each dip or step taking one second. The specimen was then dipped in tap or distilled water bath 10 times, with each dip taking 1 second. The specimen was then dipped in a Richard-Allan Hematoxylin-2 stain bath 10 times, with each dip taking 1 second. The specimen was then dipped in a fresh tap or distilled water bath 10 times, with each dip taking 10 seconds. The specimen was then dipped in a 95% ethanol bath 10 times, with each dip taking 1 second. The specimen was then dipped in a fresh tap or distilled water bath 10 times, with each dip taking 1 second. The specimen was then dipped in Richard-Allan Cytostain bath 10 times, with each dip taking 1 second. The specimen was then dipped in a fresh 95% ethanol bath 10 times, with each dip taking one second. The specimen was then dipped in a fresh 100% ethanol bath 10 times, with each dip taking 1 second. The specimen was then dipped in a fresh 100% ethanol bath, with each dip taking one second. The specimen was then dipped in a 100% xylene bath 10 times, with each step taking one second.

The specimen was then mounted and coverslip provided by means well known in the art. The finished mounted specimen was examined under the microscope and found to have an excellent stain quality with sharp and bright stain contrast, with a decrease in granularity and haziness in the background.

The overall time of the present staining method is from 100 to 150 seconds. This is generally a substantially reduced overall time for the prior art, and in combination with the equal 1 second dips/step, provides a more efficient less error prove method than previously practiced in the art.

The stains used in the present Example were:
Richard-Allan hematoxylin 2 (Cat. #7231)
Ingredients:

| | |
|---|---|
| Ethylene glycol | CAS #107-21-1 |
| Glacial Acetic Acid | CAS #64-19-7 |
| Hematoxylin | CAS #517-28-2 |
| Aluminium Sulfate | CAS #10043-01-3 |
| Sodium Iodate | CAS #7681-55-2 |

Richard-Allan Cytostain (Cat. #7511)
Ingredients:

| | |
|---|---|
| Ethyl Alcohol | CAS #64-17-5 |
| Isopropyl Alcohol | CAS #67-63-0 |
| Cytostain | |

It was found that a hematoxylin stain containing glacial acetic acid was particularly useful in providing improved clean stain background in a ThinPrep Pap test slide specimen. The aforesaid stains are available from Richard-Allan Scientific, Kalamazoo, Mich.

The alcohols useful in the present invention are the lower alcohols, and preferably ethanol. The low molecular weight organic solvent useful in the present invention is preferably an aromatic hydrocarbon. The preferred low molecular weight aromatic is xylene. The buffered formalin used in keeping solution is readily commercially available.

The present staining method provides several additional advantages including:

(1) minimized exposure to formaldehyde with concomitant avoidance of lessened immunocytochemical activity;

(2) ease of preparation of the fixative solution; and (3) avoidance of exposure to high concentrations of formaldehyde, which may alter the cell membrane protein structures and which may change the cytomorphology.

From the foregoing description it will be seen that the invention provides a novel, fast and convenient method for Pap test slide specimen staining, useful in the diagnosis and treatment of cervical cancer, and particularly adapted for large volume activity of Pap test slide specimens, for conventional pap smears and particularly ThinPrep Pap test slide specimens, with reductions in errors in specimen preparation, and with better stain contrast and improved background in the finished specimen. The foregoing described invention is, by virtue of the equal dip steps and time, readily adaptable to mechanized automated or semi-automated operations, wherein the laboratory technician is unlikely to commit error. The present method facilitates its adaption and use for automatic stainer machines.

The terms and expressions which have been used are used as terms of description and not of limitation and there is no intention in the use of such terms and expressions of excluding any equivalents of any of the features shown or described, or portions thereof. Moreover, various modifications in the preferred embodiment are possible within the scope of the claimed invention.

What is claimed is:

1. A method for staining a gynecological Pap test slide specimen comprising:

(a) fixing the slide specimen;

(b) hydrating the slide specimen from step (a);

(c) staining the slide specimen from step (b) for at least about 10 to 15 seconds;

(d) hydrating the slide specimen from step (c);

(e) staining the slide specimen from step (d) for at least about 10 to 15 seconds; and (f) dehydrating the slide specimen from step (e); wherein the total time for steps (a) through (f) is no more than about 100 to 150 seconds.

2. The method of claim 1, wherein the step (f) comprises; (f)(i) dehydrating with an alcohol for at least about 10 to 15 seconds; (f)(ii) dehydrating with an alcohol for at least about 10 to 15 seconds; and (f)(iii) dehydrating with an alcohol for at least about 10 to 15 seconds.

3. The method of claim 2, wherein steps (b) and (d) are for at least about 10 to 15 seconds.

4. The method of claim 2, wherein steps (b) through (f)(iii) comprise dipping the slide specimen for 10 to 15 times for about1 second each dip.

5. The method of claim 4, wherein step (c) comprises dipping the slide specimen in a hematoxylin stain, and step (e) comprises dipping the slide specimen in a cytostain.

6. The method of claim 5, further comprising treating the specimen from step (f) (iii) with an organic solvent.

7. The method of claim 6, wherein the organic solvent comprises xylene.

8. The method of claim 2, wherein the Pap test slide specimen is a thin preparation specimen.

9. The method of claim 2, wherein steps (f) (i) and (f) (ii) comprise dipping the slide specimen in a 95% alcohol solution, and step (f) (iii) comprises dipping the slide specimen in a 100% alcohol solution.

10. The method of claim 1, wherein the Pap test slide specimen is a thin preparation specimen.

11. A method for staining a Pap test slide specimen comprising;

(a) fixing the slide specimen;

(b) hydrating the slide specimen from step (a);

(c) staining the slide specimen from step (b) with hematoxylin;

(d) hydrating the slide specimen from step (c);

(e) staining the slide specimen from step (d) with cytostain; and (f) dehydrating the slide specimen from step (e); wherein steps (a) through (e) are about equal times of 10 to 15 seconds.

12. The method of claim 11, wherein step (a) comprises treating the slide specimen with 95% alcohol and 10% buffered formalin.

13. The method of claim 12, wherein the 10% buffered formalin and 95% alcohol are in about a 1:2 volumetric ratio.

14. The method of claim 11, wherein the hematoxylin comprises glacial acetic acid.

15. A method for staining a gynecological Pap test slide specimen comprising:

(a) fixing the slide specimen;

(b) hydrating the slide specimen from step (a);

(c) staining the slide specimen from step (b);

(d) hydrating the slide specimen from step (c);

(e) staining the slide specimen (d); and (f) dehydrating the slide specimen from step (e) in three steps (f) (i)–(f) (iii);

wherein each step (a) through (f)(iii) is for about the same time.

16. The method of claim 15, wherein the total time for steps (a) through (f) (iii) is about 100 to 150 seconds.

17. The method of claim 15, wherein each step (a) through (f) (iii) is between about 10 to 15 seconds.

* * * * *